United States Patent
Ramsden et al.

(10) Patent No.: US 6,348,592 B1
(45) Date of Patent: Feb. 19, 2002

(54) METHOD OF MAKING DIHYDROPERIMIDINE SQUARAINE COMPOUNDS

(75) Inventors: William D. Ramsden, Afton, MN (US); Louis F. Valente, Fairport, NY (US); Lori S. Bernard, Hudson, WI (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/666,234

(22) Filed: Sep. 21, 2000

(51) Int. Cl.[7] ............................................. C07D 239/70
(52) U.S. Cl. ....................................................... 544/249
(58) Field of Search ................................. 544/249, 296

(56) References Cited

U.S. PATENT DOCUMENTS

| | | | |
|---|---|---|---|
| 4,523,035 A | 6/1985 | Yanus | 564/307 |
| 4,524,219 A | 6/1985 | Law | 564/307 |
| 4,524,220 A | 6/1985 | Law | 564/307 |
| 4,525,592 A | 6/1985 | Law et al. | 564/307 |
| 4,886,722 A | 12/1989 | Law et al. | 430/59 |
| 4,922,018 A | 5/1990 | Law et al. | 564/307 |
| 5,030,537 A | 7/1991 | Law et al. | 430/135 |
| 5,360,694 A | 11/1994 | Thien et al. | 430/200 |
| 5,380,635 A | 1/1995 | Gomez et al. | 430/517 |
| 5,625,062 A | 4/1997 | Mader et al. | 544/249 |
| 5,763,134 A | 6/1998 | Busman et al. | 430/157 |
| 5,959,105 A | 9/1999 | Harada et al. | 544/231 |
| 6,063,560 A | 5/2000 | Suzuki et al. | 430/619 |

FOREIGN PATENT DOCUMENTS

| | | |
|---|---|---|
| EP | 0 748 465 B1 | 3/1998 |
| WO | WO 95/23357 | 8/1995 |

OTHER PUBLICATIONS

H. Sprenger and W. Ziegenbein, Agnew. Chem. Internat. Ed. Engl., vol. 5, 1966, pp 894.

K. Law, F. C. Bailey, and L. J. Bluett, Can. J. Chem., vol. 64, 1986, pp. 1607–1619.

K. Law and F. C. Bailey, Can. J. Chem., vol. 64, 1986, pp. 2267–2273.

K. Law and F. C. Bailey, J. Imaging Sci., vol. 31, 1987, pp. 172–177.

K. Law and F. C. Bailey, Dyes and Pigments, vol. 9, 1988, pp. 85–107.

K. Law and F. C. Bailey, J. Chem. Soc., Chem. Commun., 1990, pp. 863–864.

K. Law and F. Court Bailey, J. Chem. Soc., Chem. Comm., 1991, pp. 1156–1158

K. Law and F. C. Bailey, J. Org. Chem., vol. 57, 1992, pp. 3278–3286.

J. Chem. Soc., Chem. Commun., 1993, pp. 452–454.

*Primary Examiner*—John M. Ford
(74) *Attorney, Agent, or Firm*—J. Lanny Tucker

(57) ABSTRACT

A method to make squaraine dyes involves the reaction of 1,8-diaminonaphthalene with 1,3-dihydroxyacetone dimer in a first reaction mixture comprising the appropriate solvents to prepare a first intermediate. This first intermediate is then reacted with an organic acylating agent in the presence of a suitable solvent to form a second intermediate. Lastly, after isolation, the second intermediate is reacted with squaric acid in a particular hydroxylic solvent/nonpolar solvent mixture that dissolves squaric acid and forms a ternary azeotrope with water and the water is at least partially removed. The resulting dyes have the following general structure wherein R is an organic radical derived from the organic acylating agent.

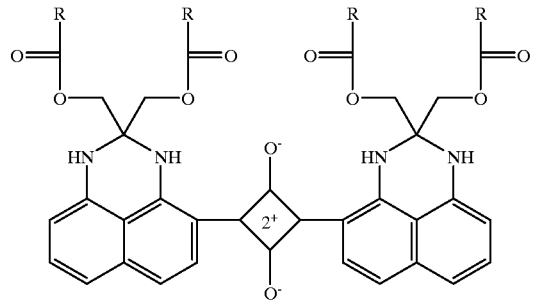

24 Claims, No Drawings

METHOD OF MAKING DIHYDROPERIMIDINE SQUARAINE COMPOUNDS

FIELD OF THE INVENTION

The present invention relates to a method for the production of organic solvent soluble squaraine dyes. More particularly, this invention relates to an improved method of using a series of reactions and reaction mixtures to provide dihydroperimidine squaraine dyes.

BACKGROUND OF THE INVENTION

Squaraine dyes are known to possess photoconductive and semi-conductive properties. These features have made then very attractive for various industrial applications such as in electrophotographic photoreceptors, organic solar cells, plasma display panels, and optical recording media, and as photopolymerization sensitizers, infrared radiation absorbing inks or paints, and acutance or antihalation dyes in photosensitive media including photothermo-graphic materials.

An early synthetic method for preparing dihydroperimidine squaraine dyes is described by Bello et al., *J. Chem. Soc., Chem. Commun.*, 1993, pp. 452–454. This method is used in EP-A-0 748,465B 1 [counterpart to WO95/23357 and U.S. Pat. No. 5,380,635 (Gomez, et al.)] for providing a squaraine dye having hexanoic acid ester substituents on the outer dihydroperimidine rings. In this method, 1,8-diaminonaphthalene and 1,3-dihydroxyacetone dimer are first reacted to form 2,2-bis(hydroxymethyl)-2,3-dihydroperimidine (the first intermediate). In the second step, the 2,2-bis(hydroxymethyl)-2,3-dihydroperimidine is reacted with squaric acid to form a bis[2,2-bis (dihydroxymethyl) dihydroperimidine] squaraine dye (the second intermediate, a tetrahydroxy squaraine compound). Finally, this tetrahydroxy squaraine intermediate is reacted with hexanoyl chloride to form the dye. U.S. Pat. No. 5,625,062 (Mader et al.) describes a number of other known synthetic methods for preparing squaraine dyes. Each of these known methods is said to suffer from various problems involving reactants, unwanted by-products, low yields, and product instability. Those problems were addressed by the synthesis described in Columns 4 and 5 therein. The synthesis described is similar to that of U.S. Pat. No. 5,380,635 (noted above). The reaction solvents and conditions were changed to improve yields.

One important feature of both U.S. Pat. No. 5,380,635 and U.S. Pat. No. 5,625,062 is the use of the expensive reagent squaric acid in the second reaction step.

U.S. Pat. No. 5,959,105 (Harada et al.) describes another method for preparing squaraine dyes having hexanoic acid ester substituents on the dihydroperimidine rings. Dipentylcarbonyloxymethyl ketone is reacted with 1,8-diaminonaphthalene to form 2,2-dipentylcarbonyloxylmethyl-2,3-dihydroperimidine. Reaction of this diester with squaric acid in a solvent mixture of butanol/toluene forms the squaraine dye having hexanoic acid ester substituents on the dihydroperimidine rings. Purification was said to be achieved by column chromatography on silica gel and elution with chloroform.

Problem To Be Solved

The synthetic methods described above have a number of disadvantages.

In both EP-A-0 748,465B 1 and U.S. Pat. No. 5,625,062 the first reaction step, preparation of 2,2-bis (hydroxymethyl)-2,3-dihydroperimidine intermediate, is carried out in an alcoholic solvent, with or without added acid catalyst. While this procedure can yield good quality product, the alcohol solvent should be completely removed before using the 2,2-bis(hydroxymethyl)-2,3-dihydroperimidine in the subsequent step. A method for preparing this intermediate while avoiding this problem would be desirable.

The second reaction in this synthesis also presents several difficulties. While the second intermediate (tetrahydroxy squaraine) can be obtained in high nominal yield, it is not obtainable in high purity (63–87% described in U.S. Pat. No. 5,625,062). No teaching is provided to purify this intermediate, and its low solubility in most solvents precludes its ready purification by such conventional methods as recrystallization or chromatography. Thus, the impurities must be carried over into the third reaction step, potentially introducing contaminants into the final reaction step.

Moreover, the second reaction step is carried out in either n-propanol (EP-A-0 748,465B1) or a mixtures of solvents including octanol or heptanol (U.S. Pat. No. 5,625,062). The use of n-propanol is undesirable because the second intermediate is difficult to separate from it. The use of mixtures of longer chain alcohols is also undesirable because of their high cost when compared with that of shorter-chain alcohols.

The thermal instability of the second intermediate is also a serious concern from a safety point of view, especially for its large-scale production. To avoid this problem, U.S. Pat. No. 5,625,062 teaches washing the second intermediate with ethanol followed by ethyl acetate. The still-damp second intermediate is then used in the subsequent step. This also introduces several practical and costly problems for large-scale production operations by exposing operators to flammable and toxic solvents or by requiring expensive safety measures.

In the third step of the synthetic method, formation of the squaraine dye, additional difficulties arise. In EP-A-0 784, 465B1, the esterification is preformed in the presence of 4-dimethylaminopyridine, an expensive and toxic reagent. In U.S. Pat. No. 5,625,062 the esterification is performed in the presence of pyridine, which while less expensive, is also toxic. Additionally, because of the low solubility of the tetrahydroxy squaraine (second intermediate) in the reaction mixture, it is usually present in the final isolated reaction product (up to 11% is noted in U.S. Pat. No. 5,625,062). This impurity diminishes the usefulness of the desired squaraine dye. The amount of insoluble intermediate remaining varies from batch to batch and requires either an additional filtration step for its removal or results in clogging of coating equipment and poor coatings containing particulates and/or exhibiting streaks.

Still another disadvantage to the synthetic methods noted above relates to the use of squaric acid in the second reaction step. Squaric acid is the most expensive raw material used in preparing squaraine dyes. Due to poor yields in these methods, and the use of squaric acid early in the synthesis, more squaric acid is required to obtain a given quantity of squaraine dye.

Although the synthesis described in U.S. Pat. No. 5,959, 105 appears to have only two reaction steps, the dipentylcarbonyloxymethyl ketone also requires preparation. U.S. Pat. No. 5,959,105 provides no teaching as to synthetic methods of its preparation, its yield, or its purity. Moreover, the purification of the final product requires use of the highly toxic solvent chloroform. Using this method for large-scale production would be costly and potentially harmful to the environment.

There is clearly a need for a more efficient method to produce dihydroperimidine squaraine dyes that avoids the difficulties and disadvantages of the known methods described above and that can be readily used in a cost effective manner in large-scale production.

SUMMARY OF THE INVENTION

The present invention provides a solution to the problems noted above with a method of making a compound comprising:

A) reacting the following Compound I with the following Compound II to form the following Compound III in a first reaction mixture comprising one or more organic solvents, wherein the molar ratio of Compound I to Compound II initially in the first reaction mixture is from about 1.5:1 to about 2:1,

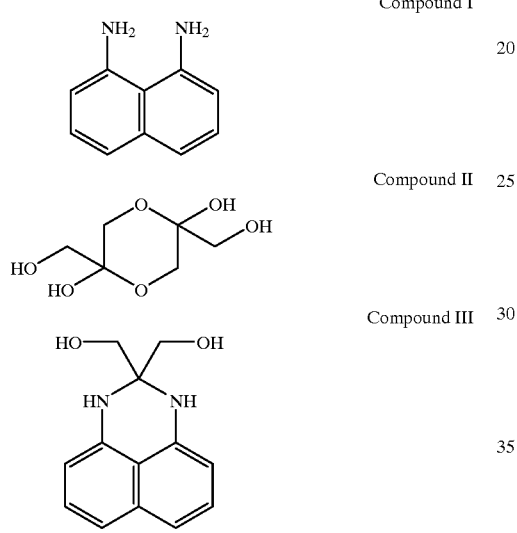

Compound I

Compound II

Compound III

B) reacting the resulting Compound III with an organic acylating agent to form the following Compound IV in the presence of one or more organic solvents, wherein the initial molar ratio of Compound III to the organic acylating agent is from about 0.4:1 to about 0.6:1, wherein R in Compounds IV and V below is a monovalent organic radical derived from the organic acylating agent,

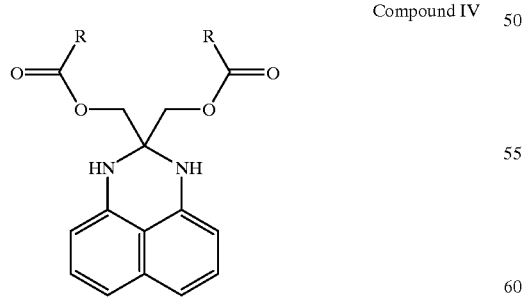

Compound IV and

C) reacting the resulting Compound IV with squaric acid to form the following Compound V in a separate reaction mixture under conditions that provide for at least partial removal of water from the separate reaction mixture, the separate reaction mixture comprising at least one hydroxylic organic solvent and at least one non-polar organic solvent, such that the squaric acid is at least partially soluble in the hydroxylic organic solvent, and the weight ratio of the hydroxylic organic solvent to the nonpolar solvent is sufficient to provide a ternary azeotrope with water,

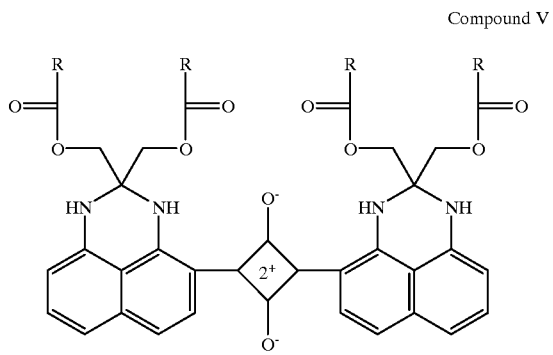

Compound V wherein the molar ratio of the Compound IV to squaric acid initially in the separate reaction mixture is at least 1.8:1.

In a preferred embodiment of this invention, a method of making a compound comprises:

A) reacting the following Compound I with the following Compound II to form the following Compound III in a first reaction mixture comprising one or more organic solvents comprising predominantly at least one alkyl ester, wherein the molar ratio of Compound I to Compound II initially in the first reaction mixture is from about 1.5:1 to about 2:1,

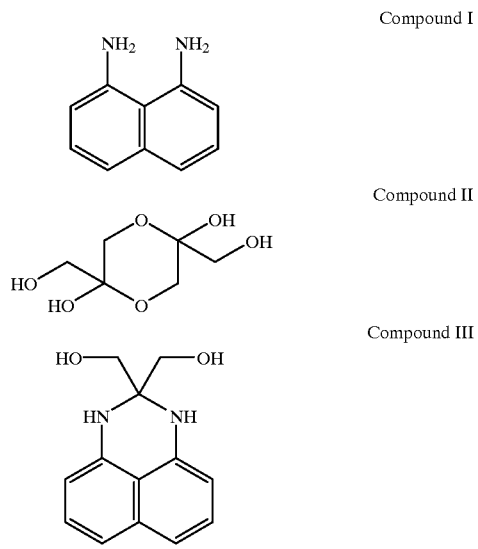

Compound I

Compound II

Compound III

B) with or without isolation, reacting the resulting Compound III with an organic acylating agent to form the following Compound IV in a second reaction mixture comprising one or more organic solvents comprising predominantly at least one alkyl ester, wherein the molar ratio of Compound III to the organic acylating agent initially in the second reaction mixture is from about 0.4:1 to about 0.6:1, wherein R in Compounds IV and V below is a monovalent organic radical derived from the organic acylating agent, Compound IV

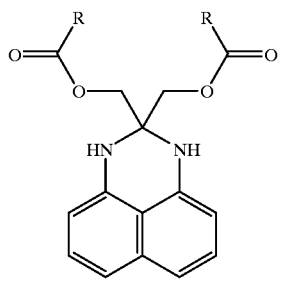

and

C) reacting the resulting Compound IV with squaric acid to form the following Compound V in a third reaction mixture under conditions that provide for at least partial removal of water from the third reaction mixture, the third reaction mixture comprising at least one hydroxylic organic solvent and at least one non-polar organic solvent, such that the squaric acid is at least partially soluble in the hydroxylic organic solvent, and the weight ratio of the hydroxylic organic solvent to the nonpolar solvent is sufficient to provide a ternary azeotrope with water, Compound V

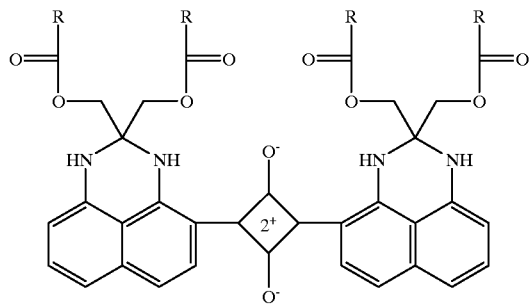

wherein the molar ratio of the Compound IV to squaric acid initially in the third reaction mixture is at least 1.9:1.

Several advantages have been achieved with the practice of the present invention compared to the several known methods for making squaraine dyes noted above. First of all, while three reactions are used instead of two (in comparison to U.S. Pat. No. 5,959,105), the reactants and solvents are readily available, inexpensive, generally less toxic and require fewer isolation procedures. The method is readily scaled up for production operations with lessened impact on the environment, reduced hazards to operators and at less expense.

With reference to the three-step methods of U.S. Pat. No. 5,625,062 and other cited references, the method of the present invention uses the expensive squaric acid reactant in the last step, thereby maximizing its incorporation into the desired final product. Required isolation techniques are reduced, and can be even avoided entirely in some embodiments of the method. For example, in embodiments wherein the same solvents such as alkyl esters are used in Steps A and B, there may be no need to isolate Compound m, the first intermediate formed in Step A before Step B can be carried out. Thus, the first and second reactions (in Steps A and B) defined herein may be carried out in the same reaction vessel having all necessary components (Compounds I and II, and organic acylating agent) present at the beginning of the method in solvents that can be used during both reactions. Alternatively, the reactants and/or different solvents for the second reaction can be added some time after the first reaction has begun, and these additional reactants and/or solvents can be added all at once, in portions or in a continual stream.

In addition, since no tetrahydroxy squaraine intermediate is produced in the second reaction of the method of this invention, fewer insoluble compounds are produced that have to be removed or carried over into the final product mixture.

All of the various features of the three reactions combine to provide a highly efficient method of making the desired squaraine dyes at increased yields and higher purity.

Lastly, the method of this invention allows the preparation of squaraine dyes having increased solubility in polar solvents, such as methyl ethyl ketone, that may be useful as coating solvents for various uses of the dyes. This reduces the potential for coating defects and coating equipment clogging from the presence of insoluble particulate materials.

The method of this invention has utility to prepare the noted squaraine dyes. Those dyes have several industrial utilities, some of which are pointed out above in the first paragraph of the Background of the Invention. A preferred utility is to use the dyes as acutance or antihalation dyes in photothermo-graphic materials, for example as described in U.S. Pat. No. 5,380,635 (noted above), and U.S. Pat. No. 6,063,560 (Suzuki et al.), both incorporated herein by reference for details regarding this preferred utility.

DETAILED DESCRIPTION OF THE INVENTION

The method of this invention generally involves the reaction of 1,8-diaminonaphthalene with 1,3-dihydroxyacetone dimer in a first reaction mixture comprising the appropriate solvents to prepare a first intermediate. This first intermediate is then reacted with an organic acylating agent in suitable solvents to form a second intermediate. Lastly, the second intermediate is reacted with squaric acid in a particular hydroxylic/nonpolar organic solvent mixture that dissolves squaric acid and forms a ternary azeotrope with water so that at least some of the water is removed during the reaction. The details of the method of this invention will be presented now in reference to the three reactions followed by discussion of optional features of the method and the working examples.

First Reaction:

In a first reaction, Compound I (1,8-diaminonaphthalene) is reacted with Compound II (1,3-dihydroxyacetone dimer) to obtain Compound III [2,2-bis(hydroxymethyl)-2,3-dihydroperimidine] that is identified herein as the "first intermediate". Compounds I and II are commercially available for example from Aldrich Chemical Company, Milwaukee, Wis.

This reaction is carried out in a first reaction mixture that includes one or more organic solvents that dissolve the reactants and from which the first intermediate can be readily isolated if necessary. In preferred embodiments, the organic solvents include predominantly at least one alkyl ester. By "predominantly" is meant that the one or more alkyl esters comprise at least 50 weight % of the weight of total solvents. Preferably, the one or more alkyl esters comprise at least 80 weight %, and more preferably at least 95 weight %, of the weight of total solvents. In the best practice of this invention, the only solvent in the first reaction mixture is an alkyl ester.

Particularly useful alkyl ester solvents include but are not limited to, alkyl acetates, alkyl propionates, and alkyl butyrates. Alkyl acetates, such as ethyl acetate, n-propyl acetate, n-butyl acetate, isopropyl acetate, and isobutyl acetate are preferred. Mixtures of these are also useful. A most preferred solvent is n-propyl acetate.

Besides alkyl esters, other organic solvents that may be used in the first reaction mixture include alcohols (such as ethanol, isopropanol, n-propanol, and n-butanol), toluene and heptane, and mixtures of any of these.

The first reaction is generally carried out until a sufficient amount of Compound III is obtained. Generally, this requires at least 60 minutes, and preferably from about 60 to about 180 minutes. Reaction temperature can be varied depending upon the solvents and the desired reaction time. Generally, the reaction temperature is at least 50° C., and preferably from about 50 to about 150° C., and more preferably from about 90 to about 101° C. A skilled worker would be able to determine the optimum reaction conditions for given solvents and desired yields.

The molar ratio of Compound I to Compound II initially in the first reaction mixture is from about 1.5:1 to about 2:1. Preferably, this molar ratio is from about 1.9:1 to about 2:1.

The first reaction may also include optional features and conditions that enhance completion of the reaction, safety or other desired results, including suitable agitation, gradual removal of solvent and water by distillation and reaction under an inert atmosphere such as nitrogen or argon.

Second Reaction:

Compound III [2,2-bis(hydroxymethyl)-2,3-dihydroperimidine] formed from the first reaction is reacted with an organic acylating agent to form Compound IV that is identified herein as the "second intermediate".

A variety of acylating agents and a variety of acylating methods can be used in the second reaction. Non-limiting examples of these agents and methods include:

a) reaction with an acid halide or an acid anhydride in the presence of a base such as an organic base (for example, an amine such as triethyl amine), a metal salt (for example, sodium acetate, sodium bicarbonate, or potassium carbonate), or a metal hydroxide (for example sodium or potassium hydroxide), b) reaction with a carboxylic acid in the presence of an acid catalyst (for example, sulfuric acid, toluene-sulfonic acid, or hydrogen chloride) usually with the removal of water (using for example, an azeotrope, molecular sieves, or an anhydrous salt), c) reaction with a carboxylic acid in the presence of a dehydrating agent (for example, a carbodiimide such as dicyclohexylcarbodiimide or diisopropylcarbodiimide), N,N'-carbonyldiimidazole, trifluoroacetic anhydride, or triphenyl phosphine with a dialkyl azodicarboxylate, and d) reaction by transesterification using a carboxylic ester (for example, methyl propionate, ethyl butyrate, or methyl hexanoate) in the presence of an acidic catalyst (for example p-toluenesulfonic acid) or a Lewis acid (such as titanium tetramethoxide) or a basic catalyst (such as sodium methoxide or potassium hydroxide).

These and additional methods can be found in "Advanced Organic Chemistry", Jerry March, $2^{nd}$ Ed., McGraw-Hill Book Co., New York, USA, 1977, pages 361–367; and in "Comprehensive Organic Functional Group Transformations", Volume 5, J. Mulzer; [A. R. Katritzky, O. Meth-Cohn, and C. W. Rees, Eds.], Elsevier Science Ltd., Oxford, UK, 1995, pages 122–139.

While mixtures of organic acylating agents can be used in the second reaction, the result would be a mixture of second intermediates that may or may not be useful in the third reaction, and may require additional isolation steps. Preferably, only a single organic acylating agent is used.

In a preferred embodiment, the organic acylating agent is an acid halide or an acid anhydride that is used in the presence of an amine. Useful organic acid halides can be any organic compound having an acid halide moiety and a suitable aliphatic or aromatic moiety that provides the "R" group in Compounds IV and V. Useful classes of organic acid halides and anhydrides include but are not limited to, aliphatic acid halides, carbocyclic aromatic acid halides, and heterocyclic acid halides. Thus, R can be any suitable substituted or unsubstituted alkyl group (branched or linear) having 1 to about 15 carbon atoms, substituted or unsubstituted cycloalkyl group having 5 to 10 carbon atoms in the cyclic system, substituted or unsubstituted aryl groups having 6 to 10 carbon atoms in the aromatic system, substituted or unsubstituted heterocyclic groups having 5 to 10 atoms in the cyclic system (including carbon, nitrogen, sulfur and oxygen atoms). Preferably, R is a substituted or unsubstituted alkyl group having 3 to 7 carbon atoms (all possible isomers).

Useful organic acid halides are chlorides, bromides, and iodides of organic acids. Useful organic acid halides include but are not limited to, acid chlorides, bromides, and iodides of pentanoic acid, hexanoic acid, heptanoic acid, octanoic acid, benzoic acid, butyric acid, and phenylacetic acid. Useful organic acid anhydrides include butyric anhydride, valeric anhydride, and hexanoic anhydride.

Aliphatic acid chlorides are preferred. Preferred acid chlorides are aliphatic acid chlorides with substituted or unsubstituted alkyl group having 3 to 7 carbon atoms. A most preferred acid chloride is n-hexanoic acid chloride.

In a preferred embodiment, the second reaction is carried out in the presence of one or more amines that catalyze the reaction and neutralize the hydrogen halide formed. Useful amines include aliphatic amines and cyclic amines. The aliphatic amines are preferred. Examples of useful amines include but are not limited to, triethylamine, tri-n-propylamine, tri-n-butylamine, pyridine, diisopropylethyl amine, N-methyl-piperdine, and N-methyl-morpholine. A most preferred amine is triethylamine.

In some embodiments, the second reaction is carried out in a distinct second reaction mixture that includes one or more organic solvents that dissolve the reactants and from which the second intermediate can be readily isolated if necessary. In such embodiments, the organic solvents preferably include predominantly at least one alkyl ester as defined for the first reaction mixture. Thus, preferably the one or more alkyl esters comprise at least 50 weight % of the weight of total solvents. More preferably, the one or more alkyl esters comprise at least 80 weight %, and most preferably at least 95 weight %, of the weight of total solvents. In the best practice of this invention, the only organic solvent in the second reaction mixture is an alkyl ester.

Particularly useful alkyl ester solvents include but are not limited to, alkyl acetates, alkyl propionates, and alkyl butyrates. Alkyl acetates, such as ethyl acetate, n-propyl acetate, n-butyl acetate, isopropyl acetate, and isobutyl acetate are preferred. Mixtures of these are also useful. A most preferred solvent is n-propyl acetate.

Besides alkyl esters, other organic solvents that may be used in the second reaction include nonhydroxylic solvents such as tetrahydrofuran (THF), toluene, dimethoxyethane, methylene chloride, and mixtures of any of these.

Alternatively, as pointed out above, the second reaction may be carried out by adding or including the components necessary for the second reaction to the first reaction mixture. Thus, the first and second reactions can be carried out sequentially or simultaneously, or even in stages (for example, first reaction, second reaction, first reaction and second reaction) by controlling addition of necessary reactants. In such embodiments, the solvents used must be compatible with both reactions, and preferably, they are the same solvents.

Irrespective of how the second reaction is carried out in relation to the first reaction, the second reaction is generally carried out until a sufficient amount of Compound IV is obtained. Generally, this requires at least 60 minutes, and preferably from about 60 to about 180 minutes. Reaction temperature can be varied depending upon the solvents and the desired reaction time. Generally, the reaction temperature is at least 0° C., and preferably from about 0 to about 50° C., and more preferably from about 5 to about 30° C. A skilled worker would be able to determine the optimum reaction conditions for given solvents and desired yields.

The molar ratio of Compound III to the organic acylating agent initially used to carry out the second reaction is from about 0.4:1 to about 0.6:1. Preferably, this molar ratio is from about 0.45:1 to about 0.50:1.

The second reaction may also include optional features and conditions that enhance completion of the reaction, safety or other desired results, including suitable agitation, and an inert atmosphere, such as nitrogen or argon.

In all preferred embodiments, the organic solvents used in the first and second reaction mixtures are the same, and most preferably, those organic solvents are alkyl esters such as ethyl acetate, n-propyl acetate, n-butyl acetate. Preferably, Compound IV is isolated from the reaction mixture (either first or second depending upon how the second reaction is carried out) before the third reaction is carried out using any suitable procedure.

Third Reaction:

Compound IV (a diester dihydroperimidine) is reacted with squaric acid to form the desired squaraine dye represented by Compound V. Squaric acid is commercially available from a number of sources such as Aldrich Chemical Company, Milwaukee, Wis.

This reaction is carried out in a separate (usually third) reaction mixture that includes one or more polar hydroxylic organic solvents and one or more nonpolar organic solvents. At least one hydroxylic organic solvent is used to dissolve squaric acid, and the hydroxylic and nonpolar organic solvents are present at a weight ratio sufficient to provide a ternary azeotrope with water. One skilled in the art would be able to readily determine the suitable weight ratio for given solvents knowing their boiling points and composition of the ternary azeotrope. Preferably, the weight ratio of nonpolar organic solvent to hydroxylic organic solvent is from about 1:2 to about 3:1, and preferably from about 1:1 to about 2:1.

By "hydroxylic" is meant that the solvent comprises one or more hydroxy groups. Useful hydroxylic organic solvents include but are not limited to, alcohols having from 3 to 7 carbon atoms (various isomers or mixtures of isomers), 2-ethoxyethanol, and 2-methoxyethanol. For purposes of this invention, hydroxylic solvents are include solvents that include one or more hydroxy groups as part of one or more carboxy groups. Such solvents include but are not limited to, acetic acid. The noted alcohols are preferred, and n-butanol, n-propanol, and n-pentanol are more preferred.

Useful nonpolar organic solvents include but are not limited to, hydrocarbons having 6 to 10 carbon atoms (all possible isomers or mixtures of isomers), chlorobenzene, and toluene. The noted hydrocarbons are preferred, and hexanes, heptanes, and cyclohexane are more preferred.

Representative organic solvent mixtures that can be used in the third reaction include but are not limited to, n-butanol/n-heptane, n-butanol/toluene, and n-butanol/cyclohexane. A mixture of n-butanol and n-heptane is most preferred.

The third reaction is carried out until a sufficient amount of Compound V is obtained, in high yield and purity. Generally, this requires at least 60 minutes, and preferably from about 60 to about 180 minutes. Reaction temperature can be varied depending upon the solvents and the desired reaction time. Generally, the reaction temperature is at the boiling point of the solvent mixture, and for preferred solvents, this means from about 80 to about 100° C. A skilled worker would be able to determine the optimum reaction conditions for given solvents and desired yields. Overall, the conditions and organic solvents are chosen so that water is at least partially, and preferably completely, removed during the reaction using conventional techniques.

The molar ratio of Compound IV to squaric acid initially in the third reaction mixture is at least 1.8:1. Preferably, this molar ratio is from about 2:1 to about 2.2:1.

The third reaction may also include optional features and conditions that enhance completion of the reaction, safety or other desired results, including suitable agitation, gradual removal of solvents and water by distillation for example, reaction in an inert atmosphere such as nitrogen or argon. Preferably, the desired squaraine dyes are isolated from the third reaction mixture using any suitable procedure such as filtration.

As would be understood by one skilled in the art, the various reaction mixtures may be heated or cooled between steps or during individual reactions to encourage the reactions to completion or to manage any exotherms. Any suitable heating and cooling means can be used. The reaction vessels to be used for each reaction are not critical although glass-lined vessels may be preferred.

In a preferred embodiment, the predominant organic solvent in both the first and second reactions is n-propyl acetate. In the second reaction, the preferred amine is triethylamine and the preferred acylating agent is a hexanoyl acid chloride (for example, n-hexanoic acid chloride). For the third reaction, the polar organic solvent is n-butanol and the nonpolar organic solvent is n-heptane.

Moreover, in preferred embodiments, the reaction conditions are as follows:

The first reaction is carried out at a temperature of from about 90 to about 101° C. for from about 60 to about 180 minutes, and Compound III can be isolated by cooling and filtration, The second reaction is carried out at a temperature of from about 5 to about 30° C. for a time of from about 60 to about 180 minutes, and Compound IV can be isolated by aqueous washing, removing solvents, adding methanol, cooling, filtering, and drying.

The third reaction is carried out at a temperature of from about 80 to about 100° C. for a time of from about 60 to about 180 minutes, and Compound V is isolated from the separate or third reaction mixture by cooling and filtration.

The preferred method of this invention, used to prepare a preferred squaraine dye, cyclobutenedilyium, 1,3-bis[2,3-dihydro-2,2-bis[[1-oxohexyl)oxy]-methyl]-1H-perimidin-4-yl]-2,4-dihydroxy-, bis(inner salt), is shown in the following Reaction Scheme:

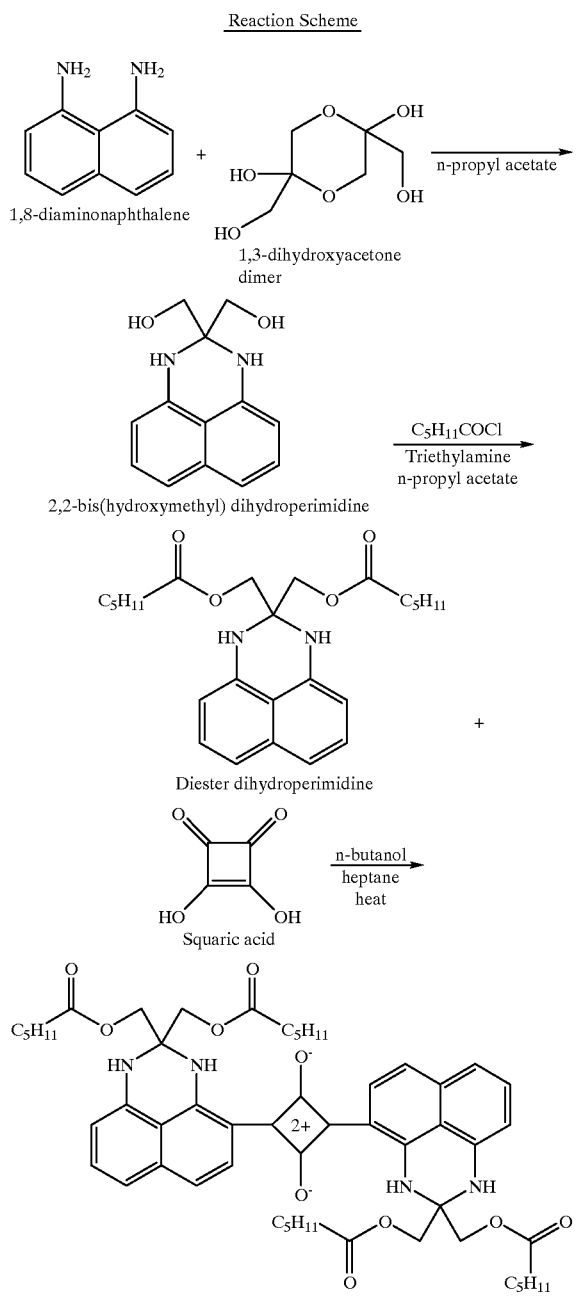

Reaction Scheme

The following examples are provided to illustrate the practice of the present invention and are not intended to be limiting in any way.

The structures of intermediate compounds and final squaraine dyes were determined using well-known spectroscopic techniques such as one-dimensional and two-dimensional (gCOSY, NOESY, gHMQC, and gHMBC), H-1 and C-13 Nuclear Magnetic Resonance Spectroscopy, Mass Spectrometry, and HPLC-MS Spectrometry. Data are in agreement with the assigned structures.

EXAMPLE 1

Synthesis of 2,2-Bis(hydroxymethyl)-2,3-dihydroperimidine in Ethanol

Into a 5-liter, round-bottomed flask equipped with mechanical stirrer, reflux condenser, nitrogen inlet, and heating mantle was put 602.45 g (3.808 mol) of 1,8-diaminonaphthalene, 361.38 g (2.0069 mol) of 1,3-dihydroxyacetone dimer, 61 mg of p-toluenesulfonic acid monohydrate, and 3 liters of anhydrous ethanol to form a first reaction mixture. After heating this reaction mixture at reflux for 1.25 hours, the mixture was cooled to room temperature. After standing overnight, the desired crystalline product (first intermediate) was recovered by suction filtration and dried. Yield 706.11 g (80.5% of theoretical).

Synthesis of 2,2-Bis(hydroxymethyl)-2,3-dihydroperimidine in n-Butyl Acetate

Into a 100 ml round bottomed flask equipped with a magnetic stirrer, Dean-Stark trap, and nitrogen inlet were put 5.29 g (33.4 mmol) of 1,8-diaminonaphthalene, 3.012 g (16.7 mmol) of 1,3-dihydroxyacetone dimer, and 50 ml of n-butyl acetate. After heating the reaction mixture at reflux for 77 minutes, the mixture was cooled to room temperature. The precipitated product was recovered by filtration and dried to yield 6.366 g of product (83% yield), mp 152.5–153.5° C.

Synthesis of 2,2-Bis(hydroxymethyl)-2,3-dihydroperimidine in 2-Methoxyethyl Acetate Into a 100 ml round bottomed flask, equipped with a magnetic stirrer, Dean-Stark trap, and nitrogen inlet were put 6.167 g (38.98 mmol) of 1,8-diaminonaphthalene, 3.511 g (19.49 mmol) of 1,3-dihydroxyacetone dimer, and 50 ml of 2-methoxyethyl acetate. After heating the reaction mixture at reflux for 72 minutes, the mixture was cooled to room temperature, 13 ml of solvent were distilled out, and reflux was continued for 57 minutes. After cooling, the precipitated product was recovered by filtration, washed with 30 ml of ethyl acetate, and dried to yield 5.873 g of product (65% yield), mp 153.5–156° C.

Synthesis of Dihydroperimidine Diester—R is n-Pentyl

Into a 5-liter, round-bottomed 3-neck flask equipped with mechanical stirrer, reflux condenser, nitrogen inlet, thermometer, and addition funnel was put 292.10 g (1.268 mol) of 2,2-bis(hydroxymethyl)-2,3-dihydroperimidine, 2.5 liters of tetrahydrofuran, and 1 liter of pyridine to form a second reaction mixture. After dissolution, this reaction mixture was cooled in an ice/water bath to 8° C. and 374 g (2.780 mol) of hexanoyl chloride in 50 ml of tetrahydrofuran were added dropwise over 42 minutes. During the addition, the temperature was allowed to rise to 21° C. After 35 minutes at room temperature, the reaction mixture was heated to 70° C. for 1 hour, and then allowed to cool to room temperature overnight. The reaction mixture was then heated at reflux for 4 hours and then about one half of the solvent was distilled out at reduced pressure (30 to 70 torr, 0.04 to 0.10 kg/cm$^2$). The reaction mixture was filtered to remove pyridinium hydrochloride, and the remainder of the solvent removed under reduced pressure, leaving about 1 liter of dark oil. To this oil was added 400 ml of ethanol, 1 liter of water, and a few seed crystals of the desired second intermediate. After stirring for 5 min, the desired product (second intermediate) crystallized. After suction filtration and air drying, the product was recrystallized from a total volume of 2.1 liters with ethanol. Filtration and air-drying gave 378.21 g (70% of theoretical) of yellow brown crystals, m.p. 75–77.5° C. Approximately 20 g of additional desired product can be obtained as a second crop by concentrating the ethanol filtrate, followed by crystallization and filtration.

Synthesis of Dihydroperimidine Diester Without Isolation of Compound III—R is n-Pentyl A mixture of 31.6 g (0.200 mol) of 1,8-diaminonaphthalene and 18.9 g (0.104 mol) of 1,3- dihydroxyacetone dimer in 400 ml of n-propyl acetate was heated to boiling for 1.5 hours, during which time 200 ml of solvent was removed by distillation. After cooling, 100 ml of n-propyl acetate and 50.0 g (0.50 mol) of triethylamine were added, the mixture further cooled to 5° C., and 62.0 g (0.461 mol) of hexanoyl chloride added over 30 minutes. After 1 hour at 20° C., 200 ml of water were added, the mixture filtered through Super Cel filter aide, the organic layer washed with 200 ml of water, the solvents removed at 30 to 50 torr (0.04 to 0.07 $kg_f/cm^2$), 400 ml of isopropanol added, and the mixture heated. Cooling, filtration, and drying yielded 65.8 g of product (77% yield).

Synthesis of Dihydroperimidine Diester—R is n-Pentyl

A mixture of 5.00 g (21.7 mmol) of 2,2-bis(hydroxymethyl)-2,3-dihydroperimidine, 5.07 g (43.0 mmol) of hexanoic acid, 9.00 g (44.0 mmol) of dicyclohexylcarbodiimide, 0.60 g (4.4 mmol) of 4-pyrrolidinopyridine, and 75 ml of diethyl ether was stirred at room temperature overnight, filtered, washed with dilute hydrochloric acid solution, followed by saturated sodium bicarbonate solution, dried over magnesium sulfate. Filtration and solvent removed at 30 to 50 torr (0.04 to 0.07 $kg_f/cm^2$), gave 7.8 g of product (85% yield).

Synthesis of Dihydroperimidine Diester—R is tert-Butyl

To a magnetically stirred mixture of 8.594 g (37.3 mmol) of 2,2-bis(hydroxymethyl)-2,3-dihydroperimidine, 9.33 g (92.2 mmol) of triethyl amine, and 60 ml of n-propyl acetate in a 250 ml round-bottomed flask, were added 10.48 g (86.9 mmol) of pivaloyl chloride dropwise over 15 minutes. After stirring at room temperature for 3 days, 50 ml of ethyl acetate were added, the mixture was washed 2 times with water and once with 40 ml of 1 M hydrochloric acid solution, dried over magnesium sulfate, and filtered, and the solvents were removed at 30 to 50 torr (0.04 to 0.07 $kg_f/cm^2$). The residue was dissolved in 200 ml of boiling methanol, cooled, and the product recovered by filtration and drying to give 8.77 g (59% yield), m.p. 172–173° C.

Synthesis of Dihydroperimidine Diester—R is Phenyl

To a magnetically stirred mixture of 8.522 g (37.01 mmol) of 2,2-bis(hydroxymethyl)-2,3-dihydroperimidine, 11.958 g (92.5 mmol) of diisopropylethyl amine, and 60 ml of n-propyl acetate in a 250 ml round bottomed flask, were added 15.79 g (85.33 mmol) of benzoyl bromide dropwise over 2 minutes. The mixture was stirred at room temperature for 18 hours, 100 ml of ethyl acetate were added, the mixture stirred an additional 24 hours. Then, 100 ml of water were added, the water layer was extracted with 100 ml of ethyl acetate, and the combined organic layers were washed with 100 ml of 1 M hydrochloric acid solution, and with 100 ml of water, and dried over magnesium sulfate. Filtration to remove drying agent was followed by solvent removal at 30 to 50 torr (0.04 to 0.07 $kg_f/cm^2$). To the resulting oil, 20 ml of toluene were added, causing it to crystallize. The product was collected by filtration and recrystallized from ethanol to give 5.543 g (34% yield), mp 166–167° C.

Synthesis of Dihydroperimidine Diester—R is n-Nonyl

To a magnetically stirred mixture of 2.015 g (8.75 mmol) of 2,2-bis(hydroxymethyl)-2,3-dihydroperimidine, 2.21 g (21.9 mmol) of triethylamine, and 15 ml of n-butyl acetate in a 250 ml round-bottomed flask, were added 3.84 g (20.1 mmol) of decanoyl chloride all at once. After stirring at room temperature for 18 hours, ethyl acetate was added, the mixture was washed 2 times with water, once with 1 M hydrochloric acid solution, and dried over magnesium sulfate. Filtration to remove drying agent was followed by solvent removal at 30 to 50 torr (0.04 to 0.07 $kg_f/cm^2$). Methanol was added to obtain 50 ml volume, the mixture cooled, and the product recovered by filtration and drying to give 2.183 g (46% yield), m.p. 59–61° C.

Synthesis of Dihydroperimidine Diester—R is Methyl

In a 100 ml round bottomed flask was put 6.027 g (26.17 mmol) of 2,2-bis(hydroxymethyl)-2,3-dihydroperimidine, 50 ml of n-butyl acetate, 8.02 g (78.52 mmol) of acetic anhydride, and 7.94 g (78.52 mmol) of triethyl amine. After heating at reflux for 3 hours, the mixture was cooled, 100 ml of water and 50 ml of ethyl acetate were added, the organic layer washed twice with water and once with saturated sodium bicarbonate solution, and dried over magnesium sulfate. Filtration to remove drying agent was followed by solvent removal at 30 to 50 torr (0.04 to 0.07 $kg_f/cm^2$). Heptane was added to the residue, which crystallized upon standing. Recrystallization from isopropanol gave 6.147 g (75% yield), m.p. 141–142° C.

Synthesis of Squaraine Dye—R is n-Pentyl

Into a 1-liter, round-bottomed 3 neck flask equipped with magnetic stirrer, Dean-Stark trap, nitrogen inlet, and thermometer was put 59.86 g (0.1401 mol) of dihydroperimidine diester (second intermediate), 8.003 g (0.07016 mol) of squaric acid, 300 ml of heptane, 300 ml of n-butanol, and 0.23 g of water to form a third reaction mixture. This reaction mixture was heated to reflux for 100 minutes, at which time the theoretical amount of water had been collected (2.8 ml). The reaction mixture was cooled at 0° C. overnight, and the resulting desired squaraine dye was recovered by suction filtration, washed with hexane, and partially air-dried. The damp product was stirred with 250 ml of methanol for 32 minutes, filtered again, and dried in vacuo to yield 36.806 g of product 56% of theoretical). The extinction coefficient of this dye at 800 nm in tetrahydrofuran was $1.67 \times 10^5$.

Synthesis of Squaraine Dye—R is tert-Butyl

Into a 25 ml round-bottomed flask were put 1.00 g (2.51 mmol) of the dihydroperimidine diester (R=tert-butyl), 143 mg (1.25 mmol) of squaric acid, 5 ml of heptane, and 5 ml of n-butanol. With magnetic stirring under nitrogen, the mixture was heated to reflux for 86 minutes. After cooling to room temperature, the product was recovered by filtration, washed with heptane, boiled with 25 ml of methanol, filtered while hot, and dried. The product squaraine dye (R is tert-butyl) was 334 mg (30% yield), $\lambda_{max}$ (tetrahydrofuran) 800 nm ($\epsilon = 2.06 \times 10^5$).

Synthesis of Squaraine Dye—R is Phenyl

Into a 50 ml round-bottomed flask were put 1.013 g (2.31 mmol) of the dihydroperimidine diester (R=phenyl), 132 mg (1.15 mmol) of squaric acid, 10 ml of heptane, and 5 ml of n-butanol. With magnetic stirring under nitrogen, the mixture was heated to reflux under a Dean-Stark trap for 120 minutes. After cooling to room temperature, the product was recovered by filtration, washed with heptane, boiled in 25 ml of methanol, filtered while hot, and dried. The product squaraine dye (R=phenyl) was 1.054 g (95% yield), $\lambda_{max}$ (tetrahydrofuran) 801 nm ($\lambda = 1.77 \times 10^5$).

Synthesis of Squaraine Dye—R is n-Nonyl

Into a 50 ml round-bottomed flask was put 1.005 g (1.865 mmol) of the dihydroperimidine diester (R=n-nonyl), 106 mg (0.932 mmol) of squaric acid, 8 ml of heptane, and 4 ml of n-butanol. With magnetic stirring under nitrogen, the mixture was heated to reflux under a Dean-Stark trap for 137 minutes. Then, 10 ml of heptane were added, the mixture was cooled to room temperature, and the product was recovered by filtration, washed with heptane, and dried. The product squaraine dye (R is n-nonyl) was 403 mg (37% yield), $\lambda_{max}$ (tetrahydrofuran) 801 nm $\epsilon$=2.14×10$^5$).

Synthesis of Squaraine Dye—R is Methyl

Into a 25 ml round bottomed flask were put 776 mg (2.47 mmol) of the dihydroperimidine diester (R=methyl), 141 mg (1.23 mmol) of squaric acid, 10 ml of heptane, and 5 ml of n-butanol. With magnetic stirring under nitrogen, the mixture was heated to reflux under a Dean-Stark trap for 101 minutes. After cooling to room temperature, the product was recovered by filtration, washed with heptane, boiled in 10 ml of methanol, and cooled. The product squaraine dye (R is methyl) was 150 mg (17% yield), $\lambda_{max}$ (tetrahydrofuran) 800 nm ($\epsilon$=1.6×10$^5$).

Synthesis of Squaraine Dye in Acetic Acid and Cyclohexane—R is n-Pentyl

A mixture of 1.005 g (2.356 mmol) of dihydroperimidine diester (R=n-pentyl), 134 mg (1.178 mmol) of squaric acid, 10 ml of acetic acid, and 3 ml of cyclohexane was heated to reflux under nitrogen under a Dean-Stark trap for 7 hours. After cooling to room temperature, 10 ml of cyclohexane were added, the mixture was filtered, the solid was washed with heptane, boiled with 12 ml of methanol, cooled, dried, and filtered to give 204 mg of product squaraine dye (R is n-pentyl) (18% yield).

Comparison of the Effect of Several Alcohols on the Yield of Squaraine Dye—R is n-Pentyl A mixture of dihydroperimidine diester (R=pentyl) and an equivalent molar amount of squaric acid was heated with stirring in a mixture of one volume of alcohol (shown below) and two volumes of heptane to reflux for 120 minutes. After cooling to 20° C., the product dye was filtered off, washed with a 1:1 mixture of the alcohol and heptane, washed with heptane, and dried to give the yield of product shown below.

| Alcohol | Yield |
| --- | --- |
| n-Propanol | 53% |
| n-Butanol | 59% |
| n-Pentanol | 58% |

EXAMPLE 2

This example illustrates a preferred method of practicing the present invention.

Synthesis of 2,2-Bis(hydroxymethyl)-2,3-dihydroperimidine

Into a 500-ml, 4-neck round bottomed flask equipped with a Teflon-coated mechanical stirrer was put 31.6 g (0.200 mol) of 1,8-diaminonaphthalene, 3 g of Super-Cel filter aide, and 200 ml of n-propyl acetate to form a first reaction mixture. This reaction mixture was stirred at room temperature for 15 minutes, then suction filtered through a pad of Super-Cel, and the pad was rinsed with 50 ml of fresh n-propyl acetate. The filtrate was transferred to a clean 500-ml, 4-neck round-bottomed flask equipped with Teflon sweep vacuum stirrer, reflux condenser, and thermometer, and 18.9 g (0.105 mol) of 1,3-dihydroxyacetone dimer added. The reaction mixture was stirred at 300 rpm and heated to reflux (95° C.) on a heating mantle for 1 hour. At this point, 100 ml of distillate was removed via short-path distillation over 1 hour. The mixture was cooled to 5° C., and the desired product (first intermediate) was collected by suction filtration and washed with 50 ml of cold n-propyl acetate. After vacuum drying overnight at 40° C., the yield of product was 38.7 g (84% of theoretical). Chromatographic analysis of the product indicated it was 99.6% pure, m.p. 158.2° C.

Synthesis of Dihydroperimidine Diester—R is n-Pentyl

Into a 500-ml, 4-neck round bottomed flask equipped with a Teflon sweep vacuum stirrer, reflux condenser, and thermometer was put 23.0 g (0.100 mol) of 2,2-bis(hydroxymethyl)-2,3-dihydroperimidine (first intermediate), 25 g (0.247 mol) of triethylamine, and 150 ml of n-propyl acetate to form a second reaction mixture. To this reaction mixture at 20° C., was added 31.3 g (0.233 mol) of n-hexanoic acid chloride over 1 hour using a syringe pump and the slurry stirred at 20° C. for an additional hour. At this point, 75 ml of water were added, the reaction mixture was stirred for 15 minutes, and the resulting layers were allowed to separate. The lower aqueous layer was decanted and the organic layer was washed with 75 ml of a 1 molar hydrochloric acid solution. The two phases were suction filtered through a Super-Cel pad to remove a brown oily interlayer and the lower aqueous layer was decanted. The organic layer was washed with 75 ml of water and the lower aqueous layer was again decanted. At this point, the organic layer was concentrated under reduced pressure (30 to 50 torr, 0.04 to 0.07 kg$_f$/cm$^2$) with heating in a 60° C. bath. To the resulting soft solid was added 200 ml of methanol and the mixture heated to 50° C. and the product dissolved. The solution was cooled to 35° C., seeded with 0.5 g of desired product (second intermediate), held one hour, cooled to 5° C., and held an additional hour. The product was collected by suction filtration, washed twice with 50 ml of cold (5° C.) methanol, and vacuum dried at 40° C. overnight to yield 37 g of product, (87% of theoretical). Chromatographic analysis of the resulting product indicated it was 99.9% pure, m.p. 78.4° C.

Synthesis of Squaraine Dye—R is n-Pentyl

Into a 500-ml, 4-necked round-bottom flask equipped with a Teflon sweep vacuum stirrer and short path still head, was placed 30 g (0.07 mol) of the second intermediate prepared above and 4 g (0.035 mol) of squaric acid in 100 ml of n-butanol and 200 ml of n-heptane to form a third reaction mixture.

The reaction mixture was heated to reflux (95° C.) and a mixture of the two organic solvents and water was removed slowly using short path distillation over three hours. After each 100 ml of distillate was removed (after about 45 minutes), 100 ml of fresh n-heptane was added back to the flask. After 400 ml of distillate was removed, 50 ml of n-butanol and 50 ml of n-heptane were added to the resulting slurry that was then heated to 80° C., and cooled slowly to 20° C. over two hours. The resulting green slurry was collected on a Buchner funnel, washed with 50 ml of a 50:50 mixture of the two organic solvents, followed by 50 ml of n-heptane alone.

After drying the filtrate in a vacuum oven at 40° C. overnight, the yield of the desired squaraine dye was 18.7 g (57% of theoretical). Analysis confirmed the structure of the desired squaraine dye to be that shown in the Reaction Scheme above.

The invention has been described in detail with particular reference to certain preferred embodiments thereof, but it will be understood that variations and modifications can be effected within the spirit and scope of the invention.

We claim:

1. A method of making a compound represented by the Structure identified as Compound V below, said method comprising:

A) reacting the following Compound I with the following Compound II to form the following Compound III in a first reaction mixture comprising one or more organic solvents, wherein the molar ratio of said Compound I to Compound II initially in said first reaction mixture is from about 1.5:1 to about 2:1,

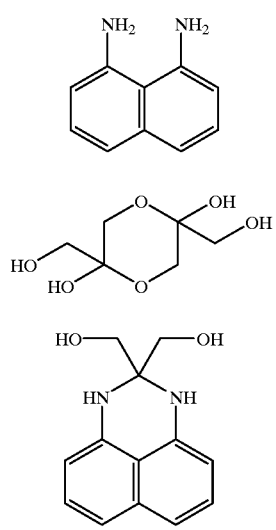

Compound I

Compound II

Compound III

B) reacting the resulting Compound III with an organic acylating agent to form the following Compound IV in the presence of one or more organic solvents, wherein the initial molar ratio of Compound III to said organic acylating agent is from about 0.4:1 to about 0.6:1, wherein R in Compounds IV and V below is a monovalent organic radical derived from said organic acylating agent,

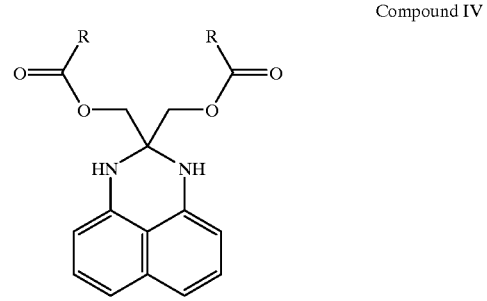

Compound IV and

C) reacting the resulting Compound IV with squaric acid to form the following Compound V in a separate reaction mixture under conditions that provide for at least partial removal of water from said separate reaction mixture, said separate reaction mixture comprising at least one hydroxylic organic solvent and at least one nonpolar organic solvent, such that squaric acid is at least partially soluble in said hydroxylic organic solvent, and the weight ratio of said hydroxylic organic solvent to said nonpolar solvent is sufficient to provide a ternary azeotrope with water,

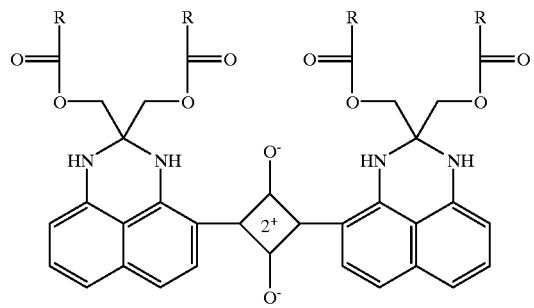

Compound V wherein the molar ratio of Compound IV to squaric acid initially in said separate reaction mixture is at least 1.8:1.

2. The method of claim 1 wherein A is carried out at a temperature of from about 50 to about 150° C. for at least 60 minutes.

3. The method of claim 1 wherein said first reaction mixture comprises at least one alkyl ester as the predominant organic solvent.

4. The method of claim 3 wherein said alkyl ester is an alkyl acetate that comprises at least 80 weight % of the total organic solvents in said first reaction mixture.

5. The method of claim 4 wherein said alkyl ester is ethyl acetate, a propyl acetate or a butyl acetate, or mixtures of any of these, that comprises at least 95 weight % of the total organic solvents in said first reaction mixture.

6. The method of claim 1 wherein said Compound III is isolated from said first reaction mixture prior to B.

7. The method of claim 1 wherein said organic acylating agent is an aliphatic acid halide that is reacted in the presence of an amine.

8. The method of claim 7 wherein said organic acid halide is an aliphatic acid chloride and said amine is an alkylamine.

9. The method of claim 8 wherein said alkylamine is triethylamine, tri-n-butylamine or diethylisopropylamine.

10. The method of claim 1 wherein at least one alkyl ester is used as the predominant organic solvent in B.

11. The method of claim 10 wherein said alkyl ester is an alkyl acetate that comprises at least 80 weight % of the total organic solvents used in B.

12. The method of claim 11 wherein said alkyl ester is ethyl acetate, a propyl acetate or a butyl acetate, or mixtures of any of these, that comprises at least 95 weight % of the total organic solvents used in B.

13. The method of claim 1 wherein A and B are carried out in the same alkyl ester solvent.

14. The method of claim 1 wherein said organic acid halide is an alkyl acid chloride.

15. The method of claim 1 wherein said Compound IV is isolated prior to Step C.

16. The method of claim 1 wherein B is carried out at a temperature of from about 0 to about 50° C. for at least 60 minutes.

17. The method of claim 1 wherein the initial molar ratio of Compound IV to squaric acid is from about 2:1 to about 2.2:1.

18. The method of claim 1 wherein C is carried out at the boiling point of said separate reaction mixture for at least 60 minutes.

19. The method of claim 1 wherein said hydroxylic organic solvent is an alcohol having 4 to 7 carbon atoms, or a mixture thereof, and said nonpolar organic solvent is a hydrocarbon having 6 to 10 carbon atoms, the weight ratio of said nonpolar solvent to said polar solvent being from about 2:1 to about 1:1 in said separate reaction mixture.

20. The method of claim 1 further comprising isolating said Compound V from said separate reaction mixture.

21. The method of claim 1 wherein the predominant organic solvent used in both A and B is n-propyl acetate, said amine is triethylamine, said organic acid halide is n-hexanoic acid chloride, said hydroxylic organic solvent is n-butanol, and said nonpolar organic solvent is heptane.

22. The method of claim 21 wherein:
A is carried out at a temperature of from about 90 to about 101° C. for from about 60 to about 180 minutes, and Compound III is isolated by cooling and filtration,
B is carried out at a temperature of from about 5 to about 30° C. for a time of from about 60 to about 180 minutes, and Compound IV is isolated by removing solvents, addition of methanol, cooling and filtration, and
C is carried out at a temperature of from about 80 to about 100° C. for a time of from about 60 to about 180 minutes, and Compound V is isolated from said separate reaction mixture by cooling and filtration.

23. A method of making a compound represented by the Structure identified as Compound V below, said method comprising:
A) reacting the following Compound I with the following Compound II to form the following Compound III in a first reaction mixture comprising one or more organic solvents comprising predominantly at least one alkyl ester, wherein the molar ratio of said Compound I to Compound II initially in said first reaction mixture is from about 1.5:1 to about 2:1, Compound I

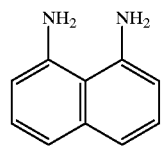

Compound II

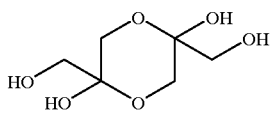

Compound III

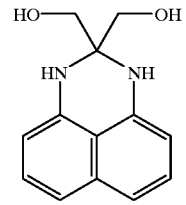

B) with or without isolation, reacting the resulting Compound III with an organic acylating agent to form the following Compound IV in a second reaction mixture comprising one or more organic solvents comprising predominantly at least one alkyl ester, wherein the molar ratio of Compound III to said organic acylating agent initially in said second reaction mixture is from about 0.4:1 to about 0.6:1,
wherein R in Compounds IV and V below is a monovalent organic radical derived from said organic acylating agent, Compound IV

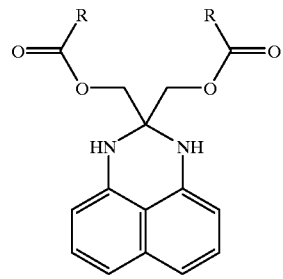

and

C) reacting the resulting Compound IV with squaric acid to form the following Compound V in a third reaction mixture under conditions that provide for at least partial removal of water from said third reaction mixture, said third reaction mixture comprising at least one hydroxylic organic solvent and at least one nonpolar organic solvent, such that squaric acid is at least partially soluble in said hydroxylic organic solvent, the weight ratio of said hydroxylic organic solvent to said nonpolar solvent is sufficient to provide a ternary azeotrope with water, Compound V

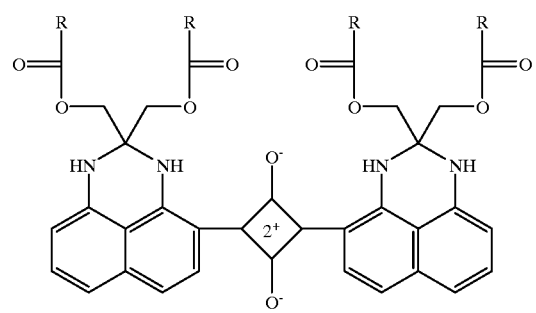

wherein the molar ratio of Compound IV to squaric acid initially in said third reaction mixture is at least 1.9:1.

24. The method of claim 23 wherein said organic acylating agent is an aliphatic acid chloride that is reacted in the presence of an amine.

* * * * *